United States Patent [19]

Holland

[11] 3,970,680
[45] July 20, 1976

[54] STORAGE-STABLE DIISOCYANATE COMPOSITIONS
[75] Inventor: John Murray Holland, Manchester, England
[73] Assignee: Imperial Chemical Industries Limited, London, England
[22] Filed: Jan. 4, 1974
[21] Appl. No.: 432,391

[52] U.S. Cl. .................... 260/453 SP; 260/453 AM
[51] Int. Cl.² ..................................... C07C 119/048
[58] Field of Search ............... 260/453 SP, 453 AM

[56] References Cited
UNITED STATES PATENTS

| | | | |
|---|---|---|---|
| 2,362,648 | 11/1944 | Lichty et al. ......................... | 260/453 |
| 3,260,702 | 7/1966 | Murakami et al. ............. | 260/453 X |
| 3,394,165 | 7/1968 | McClellan .......................... | 260/453 |
| 3,479,393 | 11/1969 | Sandridge .......................... | 260/453 |

*Primary Examiner*—Lewis Gotts
*Assistant Examiner*—Dolph H. Torrence
*Attorney, Agent, or Firm*—Cushman, Darby & Cushman

[57] ABSTRACT

Storage stable compositions comprising a diphenylmethane diisocyanate or mixture of isomers thereof and a small amount of a tertiary amine, the composition being produced by incorporating the tertiary amine into the diisocyanate.

3 Claims, No Drawings

STORAGE-STABLE DIISOCYANATE COMPOSITIONS

This invention relates to the stabilization of organic polyisocyanates in particular the stabilization of purified diphenylmethane diisocyanate by the addition of organic basic materials.

It is well known that organic polyisocyanates in particular aromatic polyisocyanates tend to discolour on storage. This discolouration is disadvantageous in that products such as polyurethanes made from discoloured organic polyisocyanates are themselves discoloured.

We have now found that discolouration of purified diphenylmethane diisocyanates may be prevented or at least considerably minimized by incorporating a small amount of an organic base into the diphenylmethane diisocyanate.

Thus according to the present invention there is provided a storage stable composition comprising a diphenylmethane diisocyanate and a small amount of organic base.

There is also provided a process for the stabilization of a diphenylmethane diisocyanate against discolouration which comprises incorporating in said diisocyanate a small amount of organic base.

The compositions of the present invention may be derived from diphenylmethane diisocyanates which have been purified by distillation or crystallization or a combination of these methods of purification but preferred compositions are those wherein the diisocyanate has been distilled at least once.

Any distilled diphenylmethane diisocyanate may be incorporated in the present composition or stabilized by the present process, including the 4,4'-isomer, the 2,4'-isomer or mixtures of these isomers containing other isomers such as the 2,2'-isomer. The 2,4'-isomer may be present, for example, up to an amount of about 40%. A diphenylmethane diisocyanate which is preferred is distilled diphenylmethane-4,4'-diisocyanate containing up to 10% of diphenylmethane-2,4'-diisocyanate and optionally small amounts, for example less than 2%, of other isomers.

Diphenylmethane diisocyanates may be made by any of the known process and isolated by distillation and/or crystallization.

Organic bases used in the compositions and process of the present invention must not contain any active hydrogen atoms, that is hydrogen atoms which would take part in the Zerewitinoff reaction. It will be readily appreciated that if such hydrogen atoms were present they would react with the isocyanate.

Examples of organic bases which may be used include tertiary amines such as triethylamine, didecyl methylamine, didodecylmethylamine, N-methyl piperidine, benzyl diethylamine, tripropylamine, tributylamine, N:N-dimethyl benzylamine, N:N'-dimethyl piperazine NN'-dilauryl piperazine, p-methyl-NN-diethyl benzylamine, p-dodecyl-N:N-diethyl benzylamine, N-methyl morpholine, N-dodecyl morpholine, N:N-dimethyl-t-butylamine, N:N-dimethyl-t-octylamine, N-methyl-1:1:3:5:5-pentamethyl piperidine, NN-diisopropyl dodecyl amine, NN'-distearyl piperazine, 1:4-diaza-(2:2:2)-bicyclooctane and N,N-dimethyl ethylamine.

As organic bases we prefer tertiary amines containing at least two alkyl, cycloalkyl or aralky groups. A preferred base is N,N-dimethyl-dodecylamine.

Organic isocyanates tend to dimerize slowly on storage forming uretedione dimers and it is known that certain organic bases for example triethylamine, accelerate the dimerisation process and it is desirable that the amount of organic base present in the compositions of this invention should not be sufficient to cause undue acceleration of the dimerisation process.

In deciding the amount of organic base to be incorporated in the present compositions, the amount of active or hydrolysable chlorine in the diphenylmethane diisocyanate may be determined and the amount of organic base equivalent to the active or hydrolysable chlorine calculated. We prefer to use not more than two equivalents of base to each equivalent of active or hydrolysable chlorine in the diisocyanate.

In many cases we have found that the amount of organic base can be based on the acidity of the diisocyanate which is generally less than the active or hydrolysable chlorine content. As a particularly preferred type of composition we prefer one in which the amount of base is from 0.5 to 1.5 equivalents per one equivalent of acidity.

Active or hydrolyzable chlorine may be conveniently determined by boiling a sample of the isocyanate under reflux with n-propanol followed by titration of the chlorine content with standard silver nitrate solution.

Acidity may be determined by stirring the isocyanate with n-propanol at room temperature and titrating the acidity to pH 7 with alcoholic potassium hydroxide. The acidity is then calculated as hydrochloric acid equivalen to the potassium hydroxide titration.

The compositions of the invention may be made by dissolving the organic base in the diisocyanate.

Pure diphenylmethane diisocyanate isomers are solids at room temperature and in the case of solid diisocyanates it is necessary to melt the diisocyanate before adding the organic base in order to obtain even distribution of the stabiliser.

The compositions of the invention are valuable starting materials for the manufacture of polyurethanes of improved colour especially solid homogeneous polyurethanes, elastomeric polyurethanes and surface coatings.

The invention is illustrated by the following Examples in which all parts and percentages are by weight except when otherwise stated.

EXAMPLE 1

A sample of freshly distilled diphenylmethane diisocyanate had 124 ppm active chlorine as determined by boiling under reflux in n-propanol followed by titration with standard silver nitrate solution. To a portion of the diisocyanate was added triethylamine equivalent to 150% of the above determined reactive chlorine. After storage in the refrigerator for one week the untreated sample was bright yellow whereas the treated sample was completely colourless. After further storage for 9 months at 0°C the treated sample was only faintly yellow whereas the control sample was orange in colour. A similar result was obtained using didecyl methyl amine as stabilizer. In neither case was an increase in rate of uretedione formation observed by infrared spectra or measurement of toluene insolubles.

Although the yellow colour often observed in distilled diphenylmethane diisocyanate is often found to be reversibly bleached by basification, acidification of the above colourless diphenylmethane diisocyanate composition after storage with triethylamine did not cause development of a yellow colour.

Similar results were obtained using the amines indicated in the following examples in place if triethylamine.

| | |
|---|---|
| Example 2 | tripropylamine |
| Example 3 | tributylamine |
| Example 4 | N:N-dimethyl benzylamine |
| Example 5 | N:N'-dimethyl piperazine |
| Example 6 | NN'-dilauryl piperazine |
| Example 7 | p-methyl -NN-diethyl benzylamine |
| Example 8 | p-dodecyl-N:N-diethyl benzylamine |
| Example 9 | N-methyl morpholine |
| Example 10 | N-dodecyl morpholine |
| Example 11 | N:N-dimethyl-t-butylamine |
| Example 12 | N:N-dimethyl-t-octylamine |
| Example 13 | N-methyl-1:1:3:5:5-pentamethyl piperidine |
| Example 14 | NN-diisopropyl dodecyl amine |
| Example 15 | NN'-distearyl piperazine |
| Example 16 | N:N-dimethyl dodecylamine |

EXAMPLE 17

To 304.4 parts of distilled diphenylmethane-4,4'-diisocyanate containing 5.3% of the 2,4'-isomer and 231 ppm of hydrolysable chlorine, there was added at 40° – 45°C with stirring, 0.20 parts of anhydrous triethylamine. The sample was allowed to cool to room temperature and solidify. After standing for 14 days the sample was essentially colourless.

A control sample of the identical diisocyanate to which no tertiary amine had been added, turned a brilliant yellow colour overnight.

EXAMPLE 18

To 505.6 parts of pure distilled diphenylmethane-4,4'-diisocyanate (containing no detectable 2,4'-isomer) having a hydrolyzable chlorine content of 26 ppm, there was added at 40°–45°C with stirring, 0.08 parts of dodecyl dimethylamine (equivalent to the hydrolysable chlorine content). The sample was cooled to room temperature and stored for 14 days, after this time it was essentially colourless.

A control sample from which the amine had been omitted stored under the same conditions turned yellow in 14 days.

EXAMPLE 19

To 519.3 parts of pure distilled diphenylmethane-4,4'-diisocyanate (no detectable 2,4'-isomer) having an acidity of 39 ppm, there was added at 40°–45°C 0.13 parts of dodecyl dimethylamine (i.e. equivalent to the acidity). The sample was stored at 0°C for 14 days and after that time was essentially colourless. A control sample from which the amine was omitted was yellow after 14 days storage at 0°C.

We claim:
1. A storage stable composition comprising a diphenylmethane diisocyanate and a tertiary amine, said tertiary amine being present in an amount of not more than two equivalents for each equivalent of hydrolyzable chlorine in said diisocyanate, wherein said tertiary amine is triethylamine, didecyl methylamine, didodecylmethylamine, N-methyl piperidine, benzyl diethylamine, tripropylamine, tributylamine, N:N-dimethyl benzylamine, N:N'-dimethyl piperazine NN'-dilauryl piperazine, p-methyl-NN-diethyl benzylamine, p-dodecyl-N:N-diethyl benzylamine, N-methyl morpholine, N-dodecyl morpholine, N:N-dimethyl-t-butylamine, N:N-dimethyl-t-octylamine, N-methyl-1:1:3:5:5-pentamethyl piperidine, NN-diisopropyl dodecyl amine, NN'-distearyl piperazine, 1:4-diaza-(2:2:2)-bicyclooctane, N,N-dimethyl ethylamine, or N,N-dimethyl-dodecylamine.

2. Process for the stabilization of a diphenylmethane diisocyanate against discolouration which comprises incorporating in said diisocyanate a tertiary amine, wherein the tertiary amine is present in an amount of not more than two equivalents for each equivalent of active or hydrolyzable chlorine in the diisocyanate, wherein said tertiary amine is triethylamine, didecyl methylamine, didodecylmethylamine, N-methyl piperidine, benzyl diethylamine, tripropylamine, tributylamine, N:N-dimethyl benzylamine, N:N'-dimethyl piperazine NN'-dilauryl piperazine, p-methyl-NN-diethyl benzylamine, p-dodecyl-N:N-diethyl benzylamine, N-methyl morpholine, N-dodecyl morpholine, N:N-dimethyl-t-butylamine, N:N-dimethyl-t-octylamine, N-methyl-1:1:3:5:5-pentamethyl piperidine, NN-diisopropyl dodecyl amine, NN'-distearyl piperazine, 1:4-diaza-(2:2:2)-bicyclooctane, N,N-dimethyl ethylamine or N,N-dimethyl-dodecylamine.

3. A composition as claimed in claim 1 wherein the tertiary amine is dodecyl dimethylamine.

* * * * *